United States Patent [19]

Tonouchi et al.

[11] Patent Number: 5,792,630

[45] Date of Patent: Aug. 11, 1998

[54] CELLULOSE-PRODUCING MICROORGANISM TRANSFORMED WITH A GENE FOR AN ENZYME INVOLVED IN SUCROSE METABOLISM

[75] Inventors: Naoto Tonouchi; Takayasu Tsuchida; Fumihiro Yoshinaga, all of Kawasaki; Sueharu Horinouchi; Teruhiko Beppu, both of Tokyo; Hideshi Yanase, Tottori; Takahisa Hayashi, Uji, all of Japan

[73] Assignee: Bio-Polymer Research Co., Ltd., Kawasaki, Japan

[21] Appl. No.: 578,536

[22] PCT Filed: May 19, 1995

[86] PCT No.: PCT/JP95/00961

§ 371 Date: Mar. 29, 1996

§ 102(e) Date: Mar. 29, 1996

[87] PCT Pub. No.: WO95/32279

PCT Pub. Date: Nov. 30, 1995

[30] Foreign Application Priority Data

May 19, 1994 [JP] Japan ............................... 6-127995
Aug. 25, 1994 [JP] Japan ............................... 6-222751

[51] Int. Cl.$^6$ ............................ C12P 19/04; C12N 1/12; C12N 1/20; C12N 15/00
[52] U.S. Cl. .............. 435/101; 435/252.1; 435/252.33; 435/320.1; 435/823; 435/193; 435/194; 435/69.1; 536/23.2; 536/27; 530/350

[58] Field of Search ................. 435/69.1, 101, 435/252.3, 252.33, 320.1, 823, 193, 194; 536/23.2, 27; 530/350

[56] References Cited

U.S. PATENT DOCUMENTS 5,079,162  1/1992  Ben-Bassat ............... 435/252.1
5,268,274  12/1993  Ben-Bassat ............... 435/69.1

OTHER PUBLICATIONS

Kita O et al. (1992) J. Fermen. Bioeng. vol. 73, No. 3, 179–184.
Kunkel et al (1987) Methods in Enzymology 154:367–382.
Arai et al. (1992) Plant Cell Physiology 33(4):503–6.
Bockman et al (1992) Mol. Gen. Genet. 235:22.
Martin et al. (1987) Mol. Gen. Genet. 208:177–184.

*Primary Examiner*—Eric Grimes
*Assistant Examiner*—Tekchand Saidha
*Attorney, Agent, or Firm*—Oblon, Spivak, McClelland, Maier & Neustadt, P.C.

[57] ABSTRACT

A method for the production of a cellulosic product, which comprises:

culturing a cellulose-producing microorganism transformed with a gene for an enzyme involved in sucrose metabolism in a medium containing sucrose, allowing the cellulosic product to be produced and accumulated in the medium, and collecting the cellulosic product. By the present method, the cellulosic product can be produced efficiently and economically.

26 Claims, 1 Drawing Sheet

CELLULOSE-PRODUCING MICROORGANISM TRANSFORMED WITH A GENE FOR AN ENZYME INVOLVED IN SUCROSE METABOLISM

This is a 371 or U.S. national stage application of PCT/JP95/00961 filed May 19, 1995.

TECHNICAL FIELD

This invention relates to a microorganism that is capable of producing a cellulosic product (referred to hereinafter as a "cellulose-producing microorganism") and transformed with a gene for an enzyme involved in sucrose metabolism, and to a method for the production of the cellulosic product (also referred to hereinafter as a "bacterial cellulose" or "BC") by using said microorganism.

BACKGROUND ART

Since BC is edible as well as tasteless and odorless, it is utilized in the food industry. BC's high dispensability in water further provides it with a lot of industrial utility value, such as to maintain moisture and viscosity of food, cosmetics or coating agents, to strengthen food materials, to improve stability of food, and to be used as low-calorie additives and an emulsion stabilizer.

BC is characterized by a sectional width of its fibrils which is smaller by two orders of magnitude than that of other kinds of cellulose such as those derived from wood pulp.

Due to such structural and physical feature of microfibril, a macerated BC has plenty of industrial utility as a strengthening agent for polymers, especially hydrophilic polymers. Products prepared by solidification of the macerated BC in the form of a lump or paper show a high elastic modulus in tension due to the above feature, and are therefore expected to have excellent mechanical properties for use in various kinds of industrial materials.

Methods for the production of cellulose by culturing cellulose-producing microorganisms such as those belonging to the genus Acetobacter have been known in prior arts such as, for example, Japanese Patent Laid-Open Application Sho 62(1987)-265990, Japanese Patent Laid-Open Application Sho 63(1988)-202394 and Japanese Patent Publication Hei 6(1994)-43443. As a nutrient medium suitable for the culture of the cellulose-producing microorganism, Schramm/Hestrin medium is known, which contains carbon source, peptone, yeast extract, sodium phosphate and citric acid (Schramm et al., J. General Biology, 11, pp.123–129, 1954). However, when cultured under shaking, or aerobic agitated condition in the above nutrient medium, especially containing sucrose as carbon source, yield in the production of cellulose will be low and production rate will not necessarily be satisfactory.

Other culture media are also known, which further contain corn steep liquor (CSL), malt extract and the like, but no one has confirmed that a particular component in such natural nutrients as peptone, yeast extract, CSL and malt extract is involved in acceleration of the cellulose production.

The nutrients known up to now as an accelerator for the cellulose production include inositol, fitinic acid and pyrroloquinoline quinone (PQQ) (Japanese Patent Publication Hei 5(1993)-1718; Mitsuo TAKAI, Japan TAPRI Journal, Vol.42, No.3, pp.237–244). However, the cellulose production obtained with the above accelerator is not sufficient, and their effects under the shaking or aerobic agitated condition have not yet been clearly revealed.

The present inventors have also found that production of the cellulosic product is increased by addition of carboxylic acids or their salts (Japanese Patent Application Hei 5(1993)-191467), invertase (Japanese Patent Application Hei 5(1993)-331491), methionine (Japanese Patent Application Hei 5(1993)-335764), a saponin (Japanese Patent Application Hei 6(1994)-214334). Furthermore, production of the cellulosic product can be also increased by using a PQQ non-generating strain (Japanese Patent Application Hei 6(1994)-127994), a sulfur agent-resistant strain (Japanese Patent Application Hei 6(1994)-151729), a pyrimidine analogue-resistant strain (Japanese Patent Application Hei 6(1994)-158201) and a DHO-DHase inhibitors-resistant strain (Japanese Patent Application Hei 6(1994)-167573). Japanese Patent Laid-Open Application Hei 4(1992)-503456 discloses a method for increasing the cellulose production by means of introduction of at least one gene originated from a cellulose synthase operon into Acetobacter strains.

DISCLOSURE OF INVENTION

An object of the present invention is to provide a novel method for the production of a cellulosic product from an economical sugar source, sucrose in an economical and efficient manner by using a cellulose-producing microorganism.

The present inventors have carried out many kinds of researches in order to accomplish the object.

Surprisingly, it has now found that the above object can be realized by transformation of the cellulose-producing microorganism with a gene for an enzyme involved in sucrose metabolism.

The present invention relates therefore to a method for the production of the cellulosic product, which comprises:

culturing the cellulose-producing microorganism transformed with the gene for the enzyme involved in sucrose metabolism in a medium containing sucrose, allowing the cellulosic product to be produced and accumulated in the medium, and collecting the cellulosic product, and to the cellulosic product which is obtainable by this method.

Thus, the present invention relates to a cellulose-producing microorganism transformed with the gene for the enzyme involved in sucrose metabolism.

Further, the present invention relates to a cellulose-producing microorganism belonging to Acetobacter, and transformed with the gene for the enzyme involved in sucrose metabolism.

Further, the present invention relates to a PQQ non-generating strain of the cellulose-producing microorganism belonging to Acetobacter, and transformed with the gene for the enzyme involved in sucrose metabolism.

Further, the present invention relates to a cellulose-producing microorganism transformed with the gene for the enzyme involved in sucrose metabolism, selected from sucrose phosphorylase, variant-type levan sucrase, sucrose synthase or a combination of sucrose phosphorylase and sucrose permease.

Thus, the present invention relates to a method for the production of the cellulosic product, which comprises:

culturing the thus transformed cellulose-producing microorganism in the medium containing sucrose, allowing the cellulosic product to be produced and accumulated in the medium, and collecting the cellulosic product, and to the cellulosic product which is obtainable by this method.

The present invention also relates to a method for improving productivity of the cellulosic product by transforming the cellulose-producing microorganism with the gene for the enzyme involved in sucrose metabolism.

The microorganism used in transformation according to the present invention includes Acetobacter strains such as *Acetobacter xylinum* subsp. *sucrofermentans* such as the BPR 2001 strain, *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, *Acetobacter xylinum* ATCC10821; Agrobacterium; Rhizobium; Sarcina, Pseudomonus, Achromobacter, Alcaligenes, Aerobacter; Azotobacter; and Zugrea; and strains derived and breeded from those strains by means of various kinds of mutagenic treatment and recombination of genes; and strains derived and created from those strains by using known mutagens such as NTG (nitrosoguanidine).

The BPR 2001 strain is preferred for creation of the transformant according to the present invention among them, taxonomic characters of which are as follows:

Morphology: rod, Gram stain: negative, Spore formability: negative, Behavior toward oxygen: aerobic, Catalase: positive, Oxidase: negative, Formation of acetic acid from ethanol: positive, Oxidation of acetates: positive, Oxidation of lactate: positive.

The PQQ non-generating strain obtained from the BPR 2001 strain is more preferred. One example of the above PQQ non-generating strain, designated the BPR 3001c was deposited at the National Institute of Bioscience and Human-Technology Agency of Industrial Science and Technology on May 2, 1994 under accession number FERM P-14297, and then transferred on May 12, 1995 to the deposit under the terms of the Budapest Treaty on the International Recognition of the Deposit of Microorganisms for the Purposes of Patent Procedure and Regulation under accession number FERM BP- 5100.

Other mutants used in the present invention as a host cell include the sulfur agent-resistant strain designated BPR 3001D, pyrimidine analogue-resistant strain designated BPR 3001I and DHO-DHase inhibitors-resistant strain designated BPR3001N were also deposited at the National Institute of Bioscience and Human-Technology Agency of Industrial Science and Technology on May 25, 1994 under accession number FERM P-14330, on Jun. 10, 1994 under accession number FERM P-14362, and on Jun. 10, 1994 under accession number FERM P-14361, respectively.

BPR 2001 was deposited at the National Institute of Bioscience and Human-Technology Agency of Industrial Science and Technology on Feb. 24, 1993 under accession number FERM P-13466, and then transferred on Feb. 7, 1994 to the deposit under the terms of the Budapest Treaty on the International Recognition of the Deposit of Microorganisms for the Purposes of Patent Procedure and Regulation under accession number FERM BP-4545.

The "enzyme involved in sucrose metabolism" in the present invention means an enzyme which may affect biosynthesis of cellulose in the cellulose-producing microorganism when sucrose is used as sugar source in its culture. As examples, there may be mentioned sucrose phosphorylase, levan sucrase, sucrose synthase, sucrose permease, invertase and sucrose phosphotransferase, their origin being not limited but selected, for example, from microorganisms, plants and animals.

Sucrose phosphorylase (EC2.4.1.7) is known to be present in a variety of microorganisms such as, for example, in *Leuconostoc mesenteroides* (Kogad, B. O., et al., Biokhimiya, 7, 93–108 (1942), *Pseudomonas saccharophila* (Doundaroff, M., J. Biol. Chem., 151, 351–361 (1943)), and *Pseudomonas putrefaciens* (Weimberg, R. et al., J. Bacteriol., 68, 381–388 (1954)).

Furthermore, the gene for sucrose phosphorylase originated from *Leuconostoc mesenteroides* has been cloned and its base sequences have been determined (Satoshi, K., et al., J. Ferment. Bioeng., Vol. 73, No.3, 179–184 (1992)).

Since *Leuconostoc mesenteroides* strain was deposited under accession number ATCC 12291, it is easily available for those skilled in the art. Accordingly, using this strain as a starting material, artisans can obtain the gene for sucrose phosphorylase in accordance with the above publication.

The above starting material is treated with phenol to prepare chromosomal DNA, which is cleaved with a restriction enzyme such as Eco RI or Sau 3AI and ligated to a plasmid such as pBR322 digested with a similar restriction enzyme. The resulting plasmid is transformed into a suitable *E. coli* such as *E. coli* DH1 and cultured on an ampicillin containing medium. A suitable oligonucleotide probe is then synthesized based on the six N-terminus amino acids sequence (Met-Glu-Ile-Gln-Asn-Lys). Said probe is radioactively labelled and used in colony hybridization of *E. coli* DH1 colonies and Southern blot analysis. Nucleotide sequencing is carried out by in vitro packaging, digestion with endonucleases and by dideoxy-chain termination method.

Alternatively, by referring to the base sequence of sucrose phosphorylase described in J. Ferment. Bioeng., Vol. 73, No.3, 179–184 (1992), those skilled in the art may obtain the sucrose phosphorylase gene by preparing a synthesized DNA and amplifying gene fragments with said synthesized DNA in PCR, or by chemically synthesizing the gene.

Levan sucrase (EC2.4.1.10) is also known to decompose and metabolize sucrose. This enzyme has two activities, (1) hydrolysis activity of sucrose into glucose and fructose, and (2) transfructosylation activity to produce glucose and levan from sucrose. The latter activity is not preferred in terms of BC production since it will produce levan as by-product.

Levan sucrase was purified from a facultative, anaerobic, Gram-negative bacterium, *Zymomonas mobilis*, and its gene was sequenced (Yanase, H., et al., Biosci. Biotech. Biochem., 56, 1335–1337 (1992) and J. Bioeng., Vol. 71, No.3, 179–191, (1993)).

The chemical treatment with nitrites or site-directed mutagenesis could produce (1) a variant-type enzyme displaying a higher transfructosylation activity, (2) a variant-type enzyme displaying a higher sucrose hydrolysis activity, and (3) a variant-type enzyme displaying both a lower transfructosylation activity and a lower sucrose hydrolysis activity, than those of the wild-type enzyme, each gene of which was also obtained (ditto).

The present inventors have now produced a novel variant-type enzyme which has a mutation site in the region associated with transfructosylation activity and shows a remarkably increased sucrose hydrolysis activity and a decreased transfructosylation activity. The structure of the gene was also revealed.

Besides, as the genes for sucrose synthase (EC2.4.1.13) and sucrose permease have been identified and sequenced, they can be advantageously used in the present invention.

The gene for the enzyme involved in sucrose metabolism, being alone or combined with others, may be introduced into a host cell by using a suitable vector or by being directly inserted into chromosome of the host cell to transform the cellulose-producing microorganism. Transformation may be carried out in any conventional manner such as electric pulse method and calcium phosphate method.

The vector suitable for use in the present invention includes seven vectors harbored by *Acetobacter aceti.* sub-sp.*xylinum* IFO.3288 strain (Japanese Patent Laid-Open Application Hei 1(1989)-199580), and those disclosed in Proc. Natl. Acad. Sci., USA, Vol. 87, pp.8130–8134 (1990) and Japanese Patent Laid-Open Application Hei 4(1992)-503456.

Besides, recombination of the genes of Acetobacter plasmids may be advantageously manipulated by using a plasmid which can be duplicated in both Acetobacter and other kinds of host cells such as *E. coli.* (referred to hereinafter as a "shuttle vector").

Some examples of the above shuttle vector are reported in Japanese Patent Laid-Open Application Hei 1(1989)-199580 and BIOTECHNOLOGY LETTERS, Vol.14, No.7 (July, 1992), pp.539–542. Japanese Patent Laid-Open Application Hei 4(1992)-503456 also shows the examples which may be used in the present invention (page 7, right and lower column, line 15 to page 8, left and upper column, line 2).

Besides, the shuttle vectors pSA19 (Tonouchi et al., Bioscience, Biotechnology and Biochemistry, Vo. 58, p.1899 (1994)), pSA7 and pK5, which were constructed by the present inventors from an endogeneous plasmid pHA4 of the BPR 2001 strain and plasmids derived from *E. coli.* such as pUC18 (PCT/JP94/00315), may be advantageously used in the present invention. These three shuttle vectors were harbored in *E. coli* JM105 strain and deposited at the National Institute of Bioscience and Human-Technology Agency of Industrial Science and Technology (1-3, Higashi, 1-chome, Tsukuba-shi, Ibaraki-ken 305, JAPAN) on Feb. 24, 1993 under accession numbers FERM P-13469, FERM P-13468 and FERM P-13467, respectively, and then transferred on Feb. 7, 1994 to the deposit under the terms of the Budapest Treaty on the International Recognition of the Deposit of Microorganisms for the Purposes of Patent Procedure and Regulation under accession numbers FERM BP-4548, FERM BP-4547, and FERM BP-4546, respectively.

Carbon sources in the culture media useful in the present production method may, besides sucrose, further include glucose, fructose, mannitol, sorbitol, galactose, maltose, erythritol, glycerin, ethyleneglycol, ethanol and the like. In addition, sucrose may be combined with dextrin hydrolysate, citrus molasses, beet molasses, squeezed juice from beet or sugar cane, juice from citrus and the like.

Nitrogen sources useful in the present production method include organic or inorganic ones such as ammonium salts comprising ammonium sulfate, ammonium chloride, ammonium phosphate; nitrates; and urea. Nitrogen-containing natural nutrients may be also used including Bact-Peptone, Bact-soytone, Yeast-Extract and Bean-Condensate. A trace amount of organic nutrients may be further added including, 2,7,9-tricarboxy-1H pyrrolo [2,3,5]-quinoline-4,5-dione.

When the mutants with nutritional requirement for amino acids is used, for examples, such required nutrients should be supplemented in the culture media. Inorganic nutrients include phosphate salts, magnesium salts, calcium salts, iron salts, manganese salts, cobalt salts, molybdate salts, hematite salts, chelete metal salts and the like.

The known accelerators for the cellulose production mentioned above may be optionally supplemented in the culture media. The pH range for the culture according to the present invention is controlled between 3 and 7, preferably around 5. The culturing temperature is kept in a range between 10° and 40° C., preferably between 25° and 35° C. oxygen supply into a culture tank may contain from 1 to 100% oxygen, desirably 21 to 80%. The contents of these components in the culture media and amounts of the microorganisms to be inoculated into the media may be optionally determined by those skilled in the art depending on the culture method to be used.

The culture according to the present invention may be carried out by any culture conditions such as static, shaking, and aerobic agitated conditions. It is one of advantages of the present invention that the cellulose productivity will not be affected even under shaking culture, or aerobic agitated conditions. The present invention may adopt any culture operation method such as batch fermentation, fed batch fermentation, repeated batch fermentation and continuous fermentation. These culture conditions and operation methods may be optionally modified.

Means for agitation may be optionally selected from any known means such as impellers, air-lift fermentors, pump-driven recirculation of the fermentor broth and any combination of these means.

The cellulosic product produced according to the present method may be collected as such, or subjected to a treatment for removing materials other than the cellulosic product, such as bacterial cells and the like.

Such impurities may be removed from the cellulosic products by, for example, washing with water, diluted acids or alkalis, dehydration under pressure; treatment with a bleach such as sodium hypochlorite and hydrogen peroxide, a lytic enzyme such as lysozyme; treatment with a surfactant such as sodium laurylsulfate and deoxycholic acid; washing with heating at from a room temperature to 200° C.; or combinations thereof.

The cellulosic products thus obtained according to the present invention means cellulose, those comprising hetero polysaccharides which contains cellulose as a main chain, or those comprising glucans such as $\beta$-1, $\beta$-3, $\beta$-1,2 and the like. The other components than cellulose in the hetero polysaccharides are six-carbon saccharides such as mannose, fructose, galactose, xylose, arabinose, rhamnose, and gluconic acid, five-carbon saccharides, organic acids and the like.

The polysaccharides may be homogeneous materials or consist of two or more polysaccharides via hydrogen bonds.

BEST MODE FOR CARRYING OUT THE INVENTION

Figure 1:
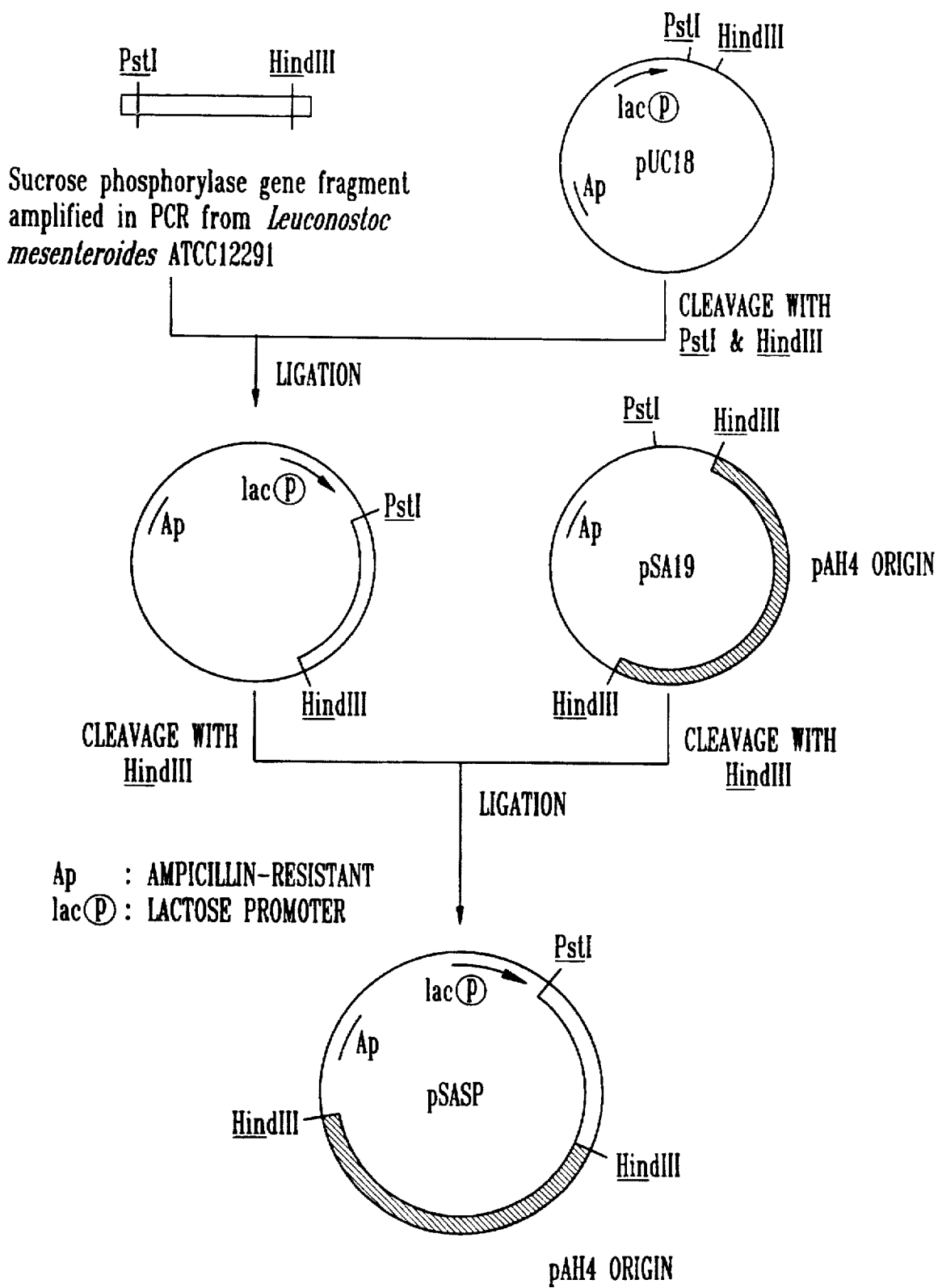
FIG. 1 represents processes of the construction of a transfomation plasmid containing the sucrose phosphorylase gene.

The present invention will be further illustrated with reference to the following examples.

EXAMPLE 1

Creation of cellulose-producing Acetobacter transformed with the sucrose phosphorylase gene Construction of plasmid to be introduced Based on the known base sequences of the sucrose phosphorylase gene of Leuconostoc mesenteroides ATCC 12291, the following DNA sequences were synthesized:

1. GTACTGCAGATTATCGCAATCGTTACAG
2. CCGAAGCTTTTGAACAGTGAGT.

A 1.8 Kb DNA fragment comprising the sucrose phosphorylase gene was amplified in PCR by using DNAs prepared from the above strain (Murray, M. G. and Thompson, W. F. Nuol., Acids, Res., 8, 4321–4325 (1980)) as templates and the above synthesized DNAs as primers.

The DNA fragment was separated by electrophoresis on agarose gel and collected. The thus collected DNA fragment was cleaved with PstI and HindIII, ligated to PstI and HindIII-digested pUC18 plasmid (Yanisch-Perron, C., et al. Gene 33, 103–119 (1985)) and to be transformed into *E. coli*. JM109 strain, followed by selection of a transformant possessing the sucrose phosphorylase gene. A plasmid comprising the same gene was prepared from the selected strain, cleaved with HindIII, ligated to HindIII-digested shuttle vector pSA19 and to be transformed into *E. coli*. JM109 strain, followed by selection of a transformant possessing both the sucrose phosphorylase gene and sequences originated from pAH4. A plasmid harbored by the selected transformant was designated pSASP, from which the plasmid was prepared again.

The above construction processes are shown in FIG. 1.

Transformation

The BPR 2001 strain was transformed with the plasmid pSASP. The BPR 2001 strain was culture in YPD medium containing 0.1% of cellulase. The bacterial cells obtained by centrifugation were washed with 10% sucrose solution, suspended into 10% sucrose solution and mixed with the plasmid DNA, which were then subjected to electric pulses transformation method by applying twenty times 1400 V electric pulse by means of a cell fusion apparatus SSH-10 (SHIMAZU CORPORATION, Japan). As a result, an ampicillin-resistant strain was obtained. Assay of the sucrose phosphorylase activity in the crude extract of the resulting tramsformant showed 0.112 U/mg protein according to the method of Kitao, S., et al., J. Ferment. Bioeng. 73, 179–184 (1992). The crude extract of a control BPR 2001 strain did not show any activity. Similarly, the transformant was prepared starting from the BPR 3001c strain.

EXAMPLE 2

Production of cellulose by the cellulose-producing Acetobacter transformed with the sucrose phosphorylase gene By using the transformant created in the above and the host strain as a control, cellulose production was carried out in a flask culture.

The culture conditions were as follows:

Flask culture

A Roux flask (750 ml volume) set up containing 100 ml of CSL-Suc medium was inoculated from glycerol stock. The cultures were grown for three days at 28° C. under non-shaking conditions. The Roux flask was vigorously shaken by hand to release cells from the resulting cellulose film and 12.5 ml of this culture medium containing the cells was inoculated into a baffle flask (500 ml long type) containing 112.5 ml of the medium followed by culture for four days at 28° C. under agitation at 180 rpm.

| CSL-Suc medium | |
|---|---|
| Component | Final conc. (mM) |
| $(NH_4)_2SO_4$ | 25 |
| $KH_2PO_4$ | 7.3 |
| $MgSO_4$ | 1.0 |
| $FeSO_4$ | 0.013 |
| $CaCl_2$ | 0.10 |
| $Na_2MoO_4$ | 0.001 |
| $ZnSO_4$ | 0.006 |
| $MnSO_4$ | 0.006 |
| $CuSO_4$ | 0.0002 |

| -continued | |
|---|---|
| Vitamin Mixture (see below) | 10 ml/l |
| Carbon Source | as specified |
| CSL | as specified |
| Anti-foam agent | 0.01 v/v % |
| Final pH | 5.0 +/−0.2 |
| (Sucrose: 40 g/l; CSL: 20 ml/l if not specified otherwise) | |

| Vitamin Mixture | |
|---|---|
| component | mg/L |
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzonic Acid | 20 |
| Folic Acid | 0.2 |
| Biotin | 0.2 |

As a result, while the BPR 2001 strain produced 1.8 g/l of cellulose, its transformant with the sucrose phosphorylase gene showed an increase of the cellulose production up to 2.5 g/l. In the case of the BPR 3001c strain, the cellulose production was significantly increased from 5.0 g/l to 6.5 g/l by the introduction of the sucrose phosphorylase gene, giving an increase of the cellulose productivity as well.

After the completion of the culture, the solid contents in the flask were collected, washed with water to remove the medium components, and treated with 1% NaOH aqueous solution for 20 min. at 110° C. to remove the bacterial cells. The resulting cellulose was washed until the washing water became approximately neutral, and dried under vacuum for 12 hours at 80° C. to weigh the dry cellulose.

Calculation of Yield (%) against the consumed sugars $$Y_{BC}=BC/(RC_{MF}-RC_{BF})*100$$

$Y_{BC}$: Yield (%) against the consumed sugars

BC: Accumulated amount of BC (g/l)

$RC_{MF}$: Sugar Concentration of the medium (g/l)

$RC_{BF}$: Sugar Concentration of the medium after the culture (g/l)

EXAMPLE 3

Creation of variant-type levan sucrase by site-directed mutagenesis

Comparison of amino acid sequences between the exocellular levan sucrase gene and exocellular invertase gene of *Zymomonas mobilis* IFO 13756 (Z6) strain revealed that $His^{297}$ at a specificity-determining region in downstreams of the levan sucrase corresponded to Asp in the invertase. An expression vector H297D comprising a variant-type enzyme gene was created from the expression vector for the levan sucrase gene, pUZE2d (Abstracts of Annual Meeting of the Society for Fermentation and Bioengineering, Japan, p.20, 1992) by site-directed mutagenesis according to the method of Kunkel, et al., Methods in Enzymology, 154, 367, (1987), which substituted Asp for $His^{297}$ of the levan sucrase by using a synthesized oligonucleotide having the sequence:

GGCATAAGTCGAATCATGACTGATCGTA as a primer.

EXAMPLE 4

Assay of the enzymatic activity of variant-type levan sucrase

E. coli. strains were transformed with the above two expression plasmids H297D and pUZE2d, which comprised the variant-type enzyme gene and wild-type enzyme gene, respectively. They were cultured, centrifuged and washed with 20 mM phosphate buffer solution to elute a crude enzyme fraction.

The activity of levan sucrase was assayed as follows: The enzyme reaction was carried out at 30° C. in 0.1 M acetate buffer solution (pH 5.0) containing 10% sucrose. Sucrose hydrolysis activity was assayed by the method of Somogy-Nelson (Tanaka et al., Agric. Biol. Chem. 42, 323–326 (1978)) which determined the amount of the sugars reduced in the above reaction. One unit of sucrose hydrolysis activity was defined as the amount of enzyme which produced 1 μmol of glucose equivalent per minute. On the other hand, transfructosylation activity was assayed by determination of each amount of glucose and fructose by means of a glucose-fructose F kit (Boehringer Manheim, GmbH).

As a result, the wild-type enzyme showed sucrose hydrolysis activity of 7.0 U/mg pr. and transfructosylation activity of 18.3%, while the variant-type enzyme showing sucrose hydrolysis activity of 57.6 U/mg pr. and transfructosylation activity of 7.4%.

EXAMPLE 5:

Production of cellulose by the cellulose-producing Acetobacter transformed with the sucrose synthase gene CDNA was constructed from MRNA prepared from hypocotyl tissue of a young seedling having germinated from *Vigna radiata* planted on vermiculite. 20 g of the hypocotyl in 50 mM tris-HCL buffer (pH 8.5) was disrupted with 100 ml of 1% SDS and 100 ml of 90% phenol, and centrifuged. The resulting supernatant was washed with phenol/chloroform (1:1) and adjusted to pH 5. RNA was precipitated at −20° C. with isopropanol of 0.6 times the amount of the supernatant, collected, dissolved into a small amount of water, and precipitated twice with 6 M lithium chloride of one twentieth the amount of the solution and ethanol of 2.5 times the amount of the solution. The thus purified RNA was subjected to chromatography on oligo d(T) cellulose to prepare mRNA. CDNA was constructed by using a cDNA synthesis kit of Amersham Co.. On the other hand, the following two DNA oligomers were prepared based on the known DNA sequences of sucrose synthase from *vigna radiata* (Arai et al., Plant Cell Physiology, Vol. 33, p.503 (1992)):

1. GAGGATCCGCCACCATGGCTAC-CGATCGTTTGACCCG
2. TCTCGGTCGACAAGCCGGTTCCT-TCATTTCTTCATCC.

The sucrose synthase gene was amplified, using cDNA prepared from Vigna radiata as template and the above DNA oligomers as primers in PCR. The amplified DNA was treated with the restriction enzymes BamHI and SalI. The resulting fragment was ligated to BamHI and SalI-digested shuttle vector pSA19 between *E. coli* and cellulose-producing strains (Tonouchi et al., Bioscience, Biotechnology and Biochemistry, Vol. 58, p.1899 (1994)) to transform *E. coli* JM 109 strain, followed by selection of a transformant harboring the desired plasmid.

The plasmid was collected from the above transformant and transformed into the cellulose-producing strain *Acetobacter xylinum* subsp. *sucrofermentans* BPR 2001 as in Example 1. The cellulose was produced in the flask culture as in Example 2. As a result, the strain having sucrose synthase introduced thereinto showed an increased cellulose production of 2.6 g/l. Similarly, the BPR 3001c strain having sucrose synthase introduced thereinto showed an increased cellulose production of 7.0 g/l, giving a significant increase of the cellulose productivity as well.

EXAMPLE 6:

Production of cellulose by the cellulose-producing Acetobacter transformed with the sucrose synthase gene and sucrose permease gene The plasmid pJBL136 comprising the sucrose permease gene of *E. coli* (J. Bockmann et al., Mol. Gen. Genet., Vol. 235, p.22 (1992)) was digested with EcoRI and SphI, blunt ended with T4DNA polymerase, ligated by T4DNA ligase to pstI linker, and digested with pstI. A DNA fragment comprising the sucrose permease gene was separated by electrophoresis on agarose gel and collected. The resulting fragment was ligated to psti-digested shuttle vector PSASP comprising the sucrose phosphrylase gene by using T4DNA ligase to transform *E. coli* JM 109 strain, followed by selection of a transformant harboring both the sucrose permease gene and sucrose phosphorylase gene. The resulting plasmid in the thus selected transformant was designated pSASPB. The plasmid pSASPB was again prepared from the transformant and transformed into the cellulose-producing strain *Acetobacter xylinum* subsp. *sucrofermentans* BPR 2001 as in Example 1. The cellulose was produced in the flask culture as in Example 2. As a result, the strain harboring the above plasmid showed an increased production of 2.7 g/l. Similarly, the BPR 3001c strain harboring the above two genes showed an increased production of 7.4 g/l, giving a significant increase of the cellulose productivity as well.

Industrial Applicability

According to the present method for the production of a cellulosic product, use of the cellulose-producing microorganism transformed with the gene for the enzyme involved in sucrose metabolism increases the yield of cellulosic product by about 20 or 30%, giving a high production of the cellulosic product. The present method for the production of the cellulosic product makes it possible to produce the cellulosic product efficiently and economically.

We claim:

1. An Acetobacter strain transformed with a gene foreign to the Acetobacter strain, wherein the foreign gene encodes an enzyme involved in sucrose metabolism.

2. The Acetobacter strain of claim 1, wherein the foreign gene is selected from the group consisting of a sucrose phosphorylase gene, a variant-type levan sucrase gene, a sucrose synthetase gene, a sucrose permease gene, an invertase gene, and a sucrose phosphotransferase gene.

3. The Acetobacter strain of claim 1, wherein the Acetobacter strain does not produce substantial quantities of pyrroloquinoline (PQQ).

4. The Acetobacter strain of claim 1, wherein the Acetobacter strain is Acetobacter xylinum.

5. The Acetobacter strain of claim 1, wherein the Acetobacter strain is selected from the group consisting of the Acetobacter strain having FERM Accession No. BP-4545 and the Acetobacter strain having FERM Accession No. BP-5100.

6. The Acetobacter strain of claim 1, wherein the foreign gene is a sucrose phosphorylase gene.

7. The Acetobacter strain of claim 1, wherein the foreign gene is a sucrose phosphorylase gene from *Leuconostoc mesenteroides*.

8. The Acetobacter strain of claim 1, wherein the foreign gene is a variant-type levan sucrase gene.

9. The Acetobacter strain of claim 1, wherein the foreign gene is a variant-type levan sucrase gene from *Zymomonas mobilis*.

10. The Acetobacter strain of claim 1, wherein the foreign gene is a sucrose synthetase gene.

11. The Acetobacter strain of claim 1, wherein the foreign gene is a sucrose synthetase gene from *Vigna radiata*.

12. The Acetobacter strain of claim 1, wherein the foreign gene is a sucrose permease gene.

13. The Acetobacter strain of claim 21, wherein the foreign gene is a sucrose permease gene from *Escherichia coli*.

14. A method for isolating a cellulosic composition comprising the steps of:
   (a) culturing, in a medium containing sucrose, an Acetobacter strain transformed with a gene foreign to the Acetobacter strain, wherein the foreign gene encodes an enzyme involved in sucrose metabolism;
   (b) allowing the cellulosic composition to be produced in the medium; and
   (c) isolating the cellulosic composition from the medium.

15. The method of claim 14, wherein the foreign gene is selected from the group consisting of a sucrose phosphorylase gene, a variant-type levan sucrase gene, a sucrose synthetase gene, a sucrose permease gene, an invertase gene, and a sucrose phosphotransferase gene.

16. The method of claim 14, wherein the Acetobacter strain does not produce substantial quantities of pyrroloquinoline (PQQ).

17. The method of claim 14, wherein the Acetobacter strain is *Acetobacter xylinum*.

18. The method of claim 14, wherein the Acetobacter strain is selected from the group consisting of the Acetobacter strain having FERM Accession No. BP-4545 and the Acetobacter strain having FERM Accession No. BP-5100.

19. The method of claim 14, wherein the foreign gene is a sucrose phosphorylase gene.

20. The method of claim 14, wherein the foreign gene is a sucrose phosphorylase gene from *Leuconostoc mesenteroides*.

21. The method of claim 14, wherein the foreign gene is a variant-type levan sucrase gene.

22. The method of claim 14, wherein the foreign gene is a variant-type levan sucrase gene from *Zymomonas mobilis*.

23. The method of claim 14, wherein the foreign gene is a sucrose synthetase gene.

24. The method of claim 14, wherein the foreign gene is a sucrose synthetase gene from *Vigna radiata*.

25. The method of claim 14, wherein the foreign gene is a sucrose permease gene.

26. The method of claim 14, wherein the foreign gene is a sucrose permease gene from *Escherichia coli*.

* * * * *

UNITED STATES PATENT AND TRADEMARK OFFICE
CERTIFICATE OF CORRECTION

PATENT NO. : 5,792,630
DATED : August 11, 1998
INVENTOR(S) : Naoto TONOUCHI et al.

It is certified that error appears in the above-identified patent and that said Letters Patent is hereby corrected as shown below:

Column 10, line 56, "synthetase" should read --synthase--.

Column 11, line 12, "synthetase" should read --synthase--.

line 14, "synthetase" should read --synthase--.

Column 12, line 2, "synthetase" should read --synthase--.

line 23, "synthetase" should read --synthase--.

line 25, "synthetase" should read --synthase--.

Signed and Sealed this

Eighteenth Day of May, 1999

*Attest:*

Q. TODD DICKINSON

*Attesting Officer*   *Acting Commissioner of Patents and Trademarks*